(12) United States Patent
Hirsbrunner et al.

(10) Patent No.: US 6,649,569 B2
(45) Date of Patent: Nov. 18, 2003

(54) COMPOSITION INTENDED FOR THE PROTECTION OF A SOLID SUBSTRATE AND ITS USE

(75) Inventors: Pierre Hirsbrunner, Corseaux (CH); Ian Horman, Blonay (CH)

(73) Assignee: Jacques Vionnet, Vessy (CH)

( * ) Notice: Subject to any disclaimer, the term of this patent is extended or adjusted under 35 U.S.C. 154(b) by 0 days.

(21) Appl. No.: 09/902,557

(22) Filed: Jul. 10, 2001

(65) Prior Publication Data

US 2002/0094937 A1 Jul. 18, 2002

(51) Int. Cl.[7] .................... A61K 31/19; A61K 31/695; A01N 55/08; A01N 55/02; A01N 37/00
(52) U.S. Cl. .................... 504/193; 504/126; 504/142; 504/190; 504/307; 514/63; 514/557
(58) Field of Search .................... 424/405; 504/121, 504/105, 193, 126, 142, 190, 307; 514/65, 731, 646, 63, 557

(56) References Cited

FOREIGN PATENT DOCUMENTS

| DD | 275433 | * | 1/1990 |
|----|--------|---|--------|
| DE | 197 03 705 A1 | | 1/1998 |
| ES | 2076064 | * | 10/1995 |
| JP | 63162561 | * | 7/1988 |
| JP | 63 085181 | | 4/1998 |
| WO | WO 00/00025 | | 1/2000 |

* cited by examiner

Primary Examiner—Alton N. Pryor
(74) Attorney, Agent, or Firm—Winston & Strawn LLP

(57) ABSTRACT

The present invention concerns a composition intended for the protection of a solid substrate against environmental attack. The composition includes at least one biocidal component and a hydrophobing agent. The composition is in the liquid phase, and the liquid is a common solvent for the hydrophobing agent and the biocidal component(s).

19 Claims, No Drawings

COMPOSITION INTENDED FOR THE PROTECTION OF A SOLID SUBSTRATE AND ITS USE

BACKGROUND

The present invention concerns a composition that is useful for protecting a solid substrate and its use.

It is common knowledge in protecting solid substrates against environmental attack to use biocides for this purpose. These compounds are agents that fight against or kill plants or other undesirable living organisms. The problem with the use of biocides is that they are very often water soluble and, as such, when exposed to bad weather, for example in the form of rains or floods, they will be diluted or washed out, with the result that the treated substrate is deprived of the protection of the compound. Thus, there is a need for improvements in this area so that biocide treated substrates can retain their effectiveness even under wet conditions.

SUMMARY OF THE INVENTION

The invention relates to a substrate treating composition for the protection of a solid substrate against environmental attack. This composition comprises at least one biocidal component, a hydrophobing agent, and a solvent for maintaining the component(s) and agent in a liquid phase. The biocidal component is present in an amount sufficient to retard growth or kill plants or similar living organisms while the hydrophobing agent is present in an amount effective to impart hydrophobicity to, or increase the hydrophobicity of, the substrate after the liquid composition is applied thereto.

Advantageously, the hydrophobing agent is a C1 to C4 alkyl siliconate compound or a siloxane polymer. A preferred siloxane polymer is a polydimethyl(H)siloxane.

The alkyl siliconate compound may be an alkali metal methyl siliconate present in an amount of about 0.005 to 5% by weight. Preferably, the alkyl siliconate compound is a sodium or potassium methyl siliconate and is present in an amount of about 0.1 to 2% by weight. If desired, a portion of the alkyl siliconate compound can be replaced with a silicate compound. This reduces the cost of the composition and improves performance as well.

The biocidal component of the composition is preferably a fungicide, an algicide, an insecticide, a rodenticide, a herbicide, a bactericide, or mixtures thereof. Generally, the biocidal component is present in an amount of about 100 to 10,000 ppm.

The solvent is preferably water or an alcohol/water mixture.

The invention also relates to a method of treating a substrate which comprises applying one of the solutions of the invention upon or within the substrate to retard growth or kill plants or similar living organisms on or in the substrate and to impart hydrophobicity to, or increase the hydrophobicity of, at least a portion of the substrate and to impart or to render hydrophobic a portion of the substrate after the liquid composition is applied thereto. The composition is typically applied to the substrate by topical application or by immersion.

Any of a wide variety of substrates can be treated according to the invention. Rock, stone, a stone-like material, a cement, a concrete or mixtures thereof, a wood, a textile, grains or cellulose-based products are all suitable for treatment.

DETAILED DESCRIPTION OF THE PREFERRED EMBODIMENTS

The present invention relates to the development of a composition for the treatment of a solid substrate which, even exposed to bad weather as described above, will conserve its biocidal protection of the substrate. A further benefit of such a composition, according to the invention, is to provide a durable protection of the substrate.

The composition of the present invention is capable of protecting a substrate against all environmental attacks. The solid substrate that is to be treated with the composition of the invention can be of all types that, when exposed to bad weather, may be subject to environmental attacks and/or attacks from rodents. For example, the nature of the substrate may be stone-like, wood, textile, or may be grains or cellulose-based products. Stone-like materials in the present description include tiles, concrete structures, bricks, sandstone and other porous stones, earthenware objects and the like. Wood, in the present description, includes construction materials (e.g., oak, beech, pine) and decorative wood (e.g., special woods for works of art, statues, furniture). Textiles include, for example, jute sacks used to contain raw materials such as coffee, cocoa, cereals or other food products. Grains include all kinds of grains attacked by rodents. Cellulose-based products include paper, paperboard and cardboard.

The hydrophobing agent is chosen among the group constituted by an alkylsiliconate compound and a siloxane polymer. When using the alkyl siliconate compound, the solvent in the composition is preferably water, while when using the siloxane polymer, the solvent is preferably an alcohol/water mixture, such as methanol/water or ethanol/water. The alkyl siliconate is preferentially methyl siliconate. The siloxane polymer is by preference polydimethyl(H)siloxane.

When an alkyl siliconate compound is utilized, part of that compound can be replaced by a silicate compound. These compounds are present in combination in amount effective to increase the hydrophobicity of the substrate after the solution is applied thereto. Advantageously, the siliconate compound is an alkali metal alkyl siliconate and the silicate compound is an alkali metal silicate, with the silicate and siliconate compounds being present in a molar ratio of about 0.5:1 to 10:1. Preferably, the siliconate compound is a alkali metal methyl siliconate and the silicate compound is an sodium or potassium hydrosoluble silicate, with the silicate and siliconate compounds being present in a molar ratio of about 1:1 to 5:1. The most preferred siliconate compound is a sodium or potassium methyl siliconate and the most preferred silicate compound is an sodium or potassium ortho or meta-silicate, with the most preferred molar ratio being about 2:1 to 3:1. In these mixtures, the siliconate compound is typically present in an amount of about 0.1 and 1% by weight and the silicate compound is typically present in an amount of about 0.01 and 5% by weight.

Depending on the end use of the composition according to the invention, different types of biocides can be included, either alone or in mixtures. The biocides are chosen among the group constituted by a fungicide, an algicide, an insecticide, a rodenticide, a herbicide and a bactericide.

The type of biocide is selected based upon the type of substrate to be protected. To protect a stone-like substrate, for example, the composition according to the invention advantageously contains a fungicide as biocidal agent. Preferred fungicides in the present invention include sodium or potassium sorbate and the copper complex of ethylene diamine tetra-acetate (EDTA), these compounds being present in the composition alone or in combination. In this case, a preferred hydrophobing agent is sodium or potassium methylsiliconate in aqueous solution.

In contrast, to protect a wooden substrate, the composition according to the invention contains an insecticide and/or a fungicide. The insecticide is preferably chosen from the group consisting of salts and chelates of active metals (Cu, Cr, Hg), fluorides, rotenoïde, pyretholdes, nitrophenols or the usual chlorine derivatives such as DDT. In this case, the hydrophobing agent is preferably polydimethyl(H)siloxane in a methanol/water solvent.

To protect textiles, for example jute cloth, against rodents, one employs a mixture of a rodenticide, such as coumarin, with polydimethyl(H)siloxane as the preferred hydrophobing agent and a methanol/water solvent.

To treat grains against rodents, one employs a rodenticide with polydimethyl(H)siloxane as the preferred hydrophobing agent.

To treat cellulose-based products, one employs a fungicide and/or a rodenticide, with polydimethyl(H)siloxane or a methylsiliconate compound as the hydrophobing agent.

The present invention also concerns the utilization of the aforementioned composition, such as by applying it to the substrate by topical application or by immersion. It is preferable to package the composition according to the invention in a concentrated form and then to dilute it appropriately before use so as to avoid excessive transport costs of the composition.

The composition according to the invention, when ready for use, is diluted to contain on the order of 0.005 to 5% by weight of the hydrophobing agent, with a preference for 0.1 to 2%, along with about 100 to 10,000 ppm of the biocidal component. The diluted composition described is applied ideally at a rate of 1 l for each 10 m$^2$ of the surface to be treated. As the composition is in liquid form, it enables the hydrophobing agents to penetrate in normal conditions to a depth on the order of about 1 to 10 mm into wood or stone-like materials, which guarantees a good and durable protection of the treated substrate.

EXAMPLES

The rest of the description is given by reference to the following specific examples which illustrate the most preferred embodiments of the invention.

Example 1

Treatment of Stone-Like Materials 25.3 kg of potassium sorbate is dissolved in 50 kg hot water. Then, to a suspension of EDTA and copper sulfate in 10 L water, 3 kg of sodium hydroxide is progressively added while simultaneously cooling the mixture. The solutions containing sorbate and complexed copper are then mixed, and the volume adjusted to 100 L by adding water. The resulting solution is mixed with 1000 kg of technical grade potassium methylsiliconate from Rhône Poulenc.

This preparation is diluted in water by a factor of 50 and applied by spraying on sandstone. After drying and reaction, the treated surface is compared to a non-treated surface as reference, after a season of exposure to the elements. The non-treated surface is humid and colonized by moss and/or lichens and or other vegetal species, whereas the treated surface exposed to the same conditions is visibly dry and free of vegetal colonization.

Example 2

Treatment of Stone-Like Materials

Example 1 is repeated, except that the sorbate and complexed copper solution is mixed with 500 kg of technical grade potassium methylsiliconate from Rhône Poulenc and 500 Kg of potassium meta silicate.

This preparation is diluted in water by a factor of 50 and applied by spraying on sandstone. After drying and reaction, the treated surface is compared to the surface treated according to Example 1 as well as to the non-treated, reference surface, after a season of exposure to the elements. The treated surface of Example 2, like that of Example 1, is visibly dry and free of vegetal colonization.

Example 3

Treatment of Wood

In 1 L of an emulsion of technical grade polydimethyl (H)siloxane from Rhône Poulenc, 10 g of sodium fluoride, 20 g of copper complex and 0.1 g of allethrin (synthetic pyrethroid) are dissolved. A solution of 10 g lindane in 0.1 L methanol is prepared, and then is added under agitation to the aqueous phase previously prepared.

An aqueous dilution at 2% of the above preparation is used for the following tests:

Four samples each of oak, beech and pine woods, dimensions 10 mm/50 mm/50 mm are soaked to saturation at the dilution described.

After drying, the samples exhibit the desired hydrophobic characteristics. They are placed, along with reference samples of untreated woods, on a surface of wood compost infested with wood louse (coleoptera) larvae and lichen spores, in a container kept at a temperature of 30° C. and with water added frequently to maintain a high humidity.

Over a 3 month period, a perfect conservation, with neither alteration nor discoloration, is observed on the treated samples, whereas all of the non-treated reference samples already show a marked degradation (although less visible for oak wood than the others) and a pronounced darkening in color.

What is claimed is:

1. A substrate treating composition for the protection of a solid substrate against environmental attack, consisting essentially of a fungicide of one of a sorbate salt, a copper complex of ethylene diamine tetra acetate, or both; a hydrophobing agent of a siliconate compound, a portion of which may optionally be replaced by a silicate; and a solvent for maintaining the fungicide(s) and agent in a liquid phase, with the fungicide(s) being present in an amount sufficient to retard growth or kill plants and the hydrophobing agent being present in an amount effective to impart hydrophobicity to, or increase the hydrophobicity of, the substrate after the composition is applied thereto.

2. The composition of claim 1, wherein the hydrophobing agent is a C1 to C4 alkyl siliconate compound.

3. The composition of claim 2, wherein the alkyl siliconate compound is an alkali metal methyl siliconate and is present in an amount of about 0.005 to 5% by weight.

4. The composition of claim 2, wherein the alkyl siliconate compound is a sodium or potassium methyl siliconate and is present in an amount of about 0.1 to 2% by weight.

5. The composition of claim 2, wherein both the alkyl silconate compound and silicate compound are present as the hydrophobic agent.

6. The composition of claim 1, wherein the fungicide is present in a total amount of about 100 to 10,000 ppm.

7. The composition of claim 1, wherein the fungicide is a mixture of the copper complex and a sodium or potassium sorbate.

8. The composition of claim 1, wherein the solvent is water or an alcohol/water mixture.

9. A method of treating a substrate which comprises applying the substrate treating composition of claim 1 upon or within the substrate to retard growth or kill plants on or in the substrate and to impart hydrophobicity to, or increase the hydrophobicity of, at least a portion of the substrate, and to impart or to render hydrophobic a portion of the substrate after the composition is applied thereto.

10. The method of claim 9, wherein the composition is applied to the substrate by topical application or by immersion.

11. The method of claim 9 wherein the substrate is rock, stone, cement, concrete or mixtures thereof, wood, textile, grains or cellulose-based products.

12. The method of claim 9 wherein the fungicide is a mixture of the copper complex and the sorbate salt, and the hydrophobing agent is potassium methylsiliconate.

13. The method of claim 9 wherein the quantity of the hydrophobing agent in the composition is about 0.005 to 5% by weight and the fungicide is present in a total amount of about 100 to 10,000 ppm.

14. A substrate treating composition for the protection of a solid substrate against environmental attack, consisting essentially of a fungicide one of a sorbate salt, a copper complex of ethylene diamine tetra acetate, or both; a hydrophobing agent of an alkali metal methyl siliconate, a portion of which may optionally be replaced by a silicate; and a solvent for maintaining the fungicide(s) and agent in a liquid phase, with the fungicide(s) being present in an amount sufficient to retard growth or kill plants and the hydrophobing agent being present in an amount effective to impart hydrophobicity to, or increase the hydrophobicity of, the substrate after the composition is applied thereto.

15. The composition of claim 14, wherein the fungicide is a mixture of the copper complex and a sodium or potassium methyl sorbate and the hydrophobing agent is potassium methyl siliconate.

16. The composition of claim 14, wherein both the methyl silconate compound and silicate compound are present as the hydrophobic agent.

17. A method of treating a substrate which comprises applying the substrate treating composition of claim 15 upon or within the substrate to retard growth or kill plants on or in the substrate and to impart hydrophobicity to, or increase the hydrophobicity of, at least a portion of the substrate, and to impart or to render hydrophobic a portion of the substrate after the composition is applied thereto.

18. A substrate treating composition for the protection of a solid substrate against environmental attack, consisting essentially of a fungicide of one of a sorbate salt, a copper complex of ethylene diamine tetra acetate, or both, optionally in combination with an insecticide which is a salt or a chelate of an active metal or a flouride; a hydrophobing agent of a siliconate compound, a portion of which may optionally be replaced by a silicate; and a solvent for maintaining the fungicide(s) and agent in a liquid phase, with the fungicide(s) being present in an amount sufficient to retard growth or kill plants and the hydrophobing agent being present in an amount effective to impart hydrophobicity to, or increase the hydrophobicity of, the substrate after the composition is applied thereto.

19. A method of treating a substrate which comprises applying the substrate treating composition of claim 18 upon or within the substrate to retard growth or kill plants on or in the substrate and to impart hydrophobicity to, or increase the hydrophobicity of, at least a portion of the substrate, and to impart or to render hydrophobic a portion of the substrate after the composition is applied thereto.

* * * * *

UNITED STATES PATENT AND TRADEMARK OFFICE
CERTIFICATE OF CORRECTION

PATENT NO. : 6,649,569 B2
DATED : November 18, 2003
INVENTOR(S) : Hirsbrunner et al.

It is certified that error appears in the above-identified patent and that said Letters Patent is hereby corrected as shown below:

<u>Column 4,</u>
Line 64, delete "silconate" and insert -- siliconate --.

<u>Column 6,</u>
Line 6, delete "silconate" and insert -- siliconate --; and
Line 20, delete "flouride" and insert -- fluoride --.

Signed and Sealed this

Seventeenth Day of February, 2004

JON W. DUDAS
*Acting Director of the United States Patent and Trademark Office*